(12) United States Patent
Iten

(10) Patent No.: US 7,947,442 B2
(45) Date of Patent: May 24, 2011

(54) APPARATUS FOR EMITTING AND DETECTING LIGHT IN A NUCLEIC ACID AMPLIFICATION REACTION

(75) Inventor: Roger Iten, Ebikon (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 86 days.

(21) Appl. No.: 12/033,711

(22) Filed: Feb. 19, 2008

(65) Prior Publication Data

US 2009/0068747 A1    Mar. 12, 2009

(30) Foreign Application Priority Data

Feb. 21, 2007  (EP) ..................................... 07102771

(51) Int. Cl.
*G01N 23/00* (2006.01)
*C12M 1/34* (2006.01)

(52) U.S. Cl. ... 435/6; 435/287.2; 435/288.7; 422/82.05; 422/82.07; 436/164; 436/172; 250/459.1; 250/461.1; 250/461.2

(58) Field of Classification Search .................. 436/164, 436/172; 250/458.1, 459.1, 461.1, 461.2; 356/320; 435/6, 287.2, 288.7; 422/82.07, 422/82.05
See application file for complete search history.

(56) References Cited

U.S. PATENT DOCUMENTS

| | | | | |
|---|---|---|---|---|
| 4,477,190 A | * | 10/1984 | Liston et al. | 356/418 |
| 6,369,893 B1 | * | 4/2002 | Christel et al. | 356/417 |
| 6,498,335 B2 | * | 12/2002 | Modlin et al. | 250/214 SW |
| 7,307,802 B2 | * | 12/2007 | Unger | 359/793 |
| 7,906,072 B2 | * | 3/2011 | Unger et al. | 422/82.05 |
| 2005/0030534 A1 | | 2/2005 | Oldham et al. | |
| 2006/0202133 A1 | * | 9/2006 | Ok et al. | 250/458.1 |
| 2007/0037272 A1 | * | 2/2007 | Beatty et al. | 435/287.2 |
| 2008/0280331 A1 | * | 11/2008 | Davies et al. | 435/91.2 |

FOREIGN PATENT DOCUMENTS

| | | |
|---|---|---|
| EP | 0953838 A1 | 11/1999 |
| EP | 1688734 A1 | 8/2006 |
| WO | WO 83/00384 A1 | 2/1983 |

OTHER PUBLICATIONS

PCT, EP 07102771, PCT Search Report, Jun. 15, 2007.

* cited by examiner

*Primary Examiner* — Jill Warden
*Assistant Examiner* — Dwan A Gerido
(74) *Attorney, Agent, or Firm* — Rhea C. Nersesian

(57) ABSTRACT

Subject of the present invention is to provide an apparatus, an instrument, and a method particularly useful in multiplex PCR applications permitting short sample measuring times of many samples combined with high sensitivity.

8 Claims, 8 Drawing Sheets

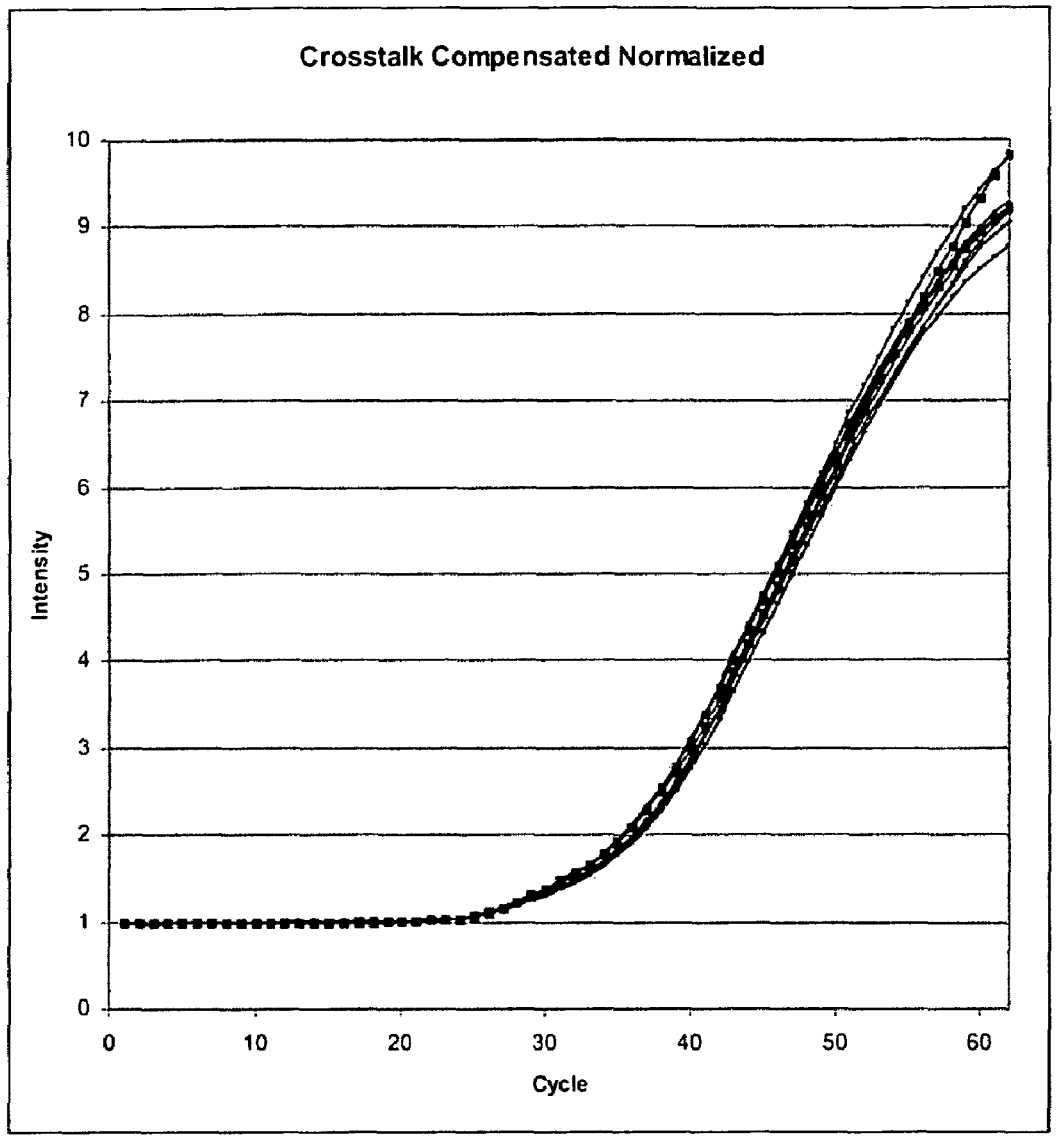

FIGURE 8

| Measurement Step | Reaction Region 1 | Reaction Region 2 | Reaction Region 3 | Reaction Region 4 | Reaction Region 5 | Reaction Region 6 | Reaction Region 7 | Reaction Region 8 | Reaction Region 9 | Reaction Region 10 | Reaction Region 11 | Reaction Region 12 |
|---|---|---|---|---|---|---|---|---|---|---|---|---|
| 1 | Channel1 | Channel1 | Channel6 | Channel6 | Channel5 | Channel5 | Channel4 | Channel4 | Channel3 | Channel3 | Channel2 | Channel2 |
| 2 | Channel2 | Channel2 | Channel1 | Channel1 | Channel6 | Channel6 | Channel5 | Channel5 | Channel4 | Channel4 | Channel3 | Channel3 |
| 3 | Channel3 | Channel3 | Channel2 | Channel2 | Channel1 | Channel1 | Channel6 | Channel6 | Channel5 | Channel5 | Channel4 | Channel4 |
| 4 | Channel4 | Channel4 | Channel3 | Channel3 | Channel2 | Channel2 | Channel1 | Channel1 | Channel6 | Channel6 | Channel5 | Channel5 |
| 5 | Channel5 | Channel5 | Channel4 | Channel4 | Channel3 | Channel3 | Channel2 | Channel2 | Channel1 | Channel1 | Channel6 | Channel6 |
| 6 | Channel6 | Channel6 | Channel5 | Channel5 | Channel4 | Channel4 | Channel3 | Channel3 | Channel2 | Channel2 | Channel1 | Channel1 |

FIGURE 9

APPARATUS FOR EMITTING AND DETECTING LIGHT IN A NUCLEIC ACID AMPLIFICATION REACTION

CROSS-REFERENCES TO RELATED APPLICATIONS

The present application claims the benefit of EP Appl. No. 07102771.8 filed Feb. 21, 2007, the entire contents of which is hereby incorporated herein by reference in its entirety.

FIELD OF THE INVENTION

Subject of the present invention is an apparatus for emitting and detecting light, an instrument for amplifying and detecting nucleic acids comprising an apparatus for emitting and detecting light and a method for detecting particular specimens (e.g., nucleic acids) in a sample using the instrument.

BACKGROUND OF THE INVENTION

The invention is particularly useful in the field of health care as well as research in biological and medical science, particularly in nucleic acid analysis, gene quantification and genotyping, where reliable analysis of samples for components contained therein is needed. Monitoring chemical reactions by the use of optical systems is well known, for example in molecular diagnostics, where chemical reactions involving nucleic acids are detected and quantified by fluorescent dyes (e.g. propidium iodide, cybergreen, acridine orange) that intercalate between the stacked bases at the centre of the DNA double helix or where specific products of the chemical reaction are detected and quantified by oligonucleotides labeled with compounds such as fluorescein, rhodamine or cyanine dyes where these labeled oligonucleotides specifically hybridize to target DNA sequences. An important aspect of such chemical reactions is monitoring the reaction by exciting the dyes via beams of light of specific wavelengths and measuring the light emitted by these dyes. Precision in these steps is a prerequisite for the accuracy of such methods.

The polymerase chain reaction (PCR) has revolutionized the field of nucleic acid treatment, particularly the analysis of nucleic acids, by providing a tool to increase the amount of nucleic acids of a particular sequence from negligible to detectable amounts. PCR is described e.g. in EP 0201184 and EP 0200362. An instrument for performing PCR in a controlled manner on samples in tubes by heating and cooling an extended metal block is disclosed e.g. in EP 0236069.

More recently improved and more powerful PCR techniques have been developed. Quantitative real time PCR is a technique used to simultaneously amplify and quantify a specific part of a given DNA molecule. It is used to determine whether or not a specific sequence is present in the sample and if present, the number of copies in the sample can be quantified. Two common methods of quantification are the use of fluorescent dyes that intercalate with double-strand DNA and modified DNA oligonucleotide probes that fluoresce when hybridized with a complementary DNA.

Furthermore, multiplex PCR techniques which enable amplification of two or more products in parallel in a single reaction tube, have been developed. These techniques may be widely used in genotyping applications and different areas of DNA testing in research, forensic, and diagnostic laboratories. Multiplex PCR can also be used for qualitative and semi-quantitative gene expression analysis using cDNA originating from a variety of eukaryotic and prokaryotic sources as a starting template.

Various instruments for performing, detecting, and monitoring such methods are known in the art. The Roche Cohas® TaqMan® instrument (see e.g., EP 0953837) and the Roche Lightcycler® 480 instrument make use of a white light source for providing excitation beams to a sample. Using a conventional white light source as an excitation light source is disadvantageous, as the lifespan of such white light sources generally is below 1000 hours of operation leading to increased maintenance efforts and costs. Furthermore, the spectral power of some white light sources (particularly halogen bulbs) is rather low in the desirable blue range, having only limited energy for exciting the sample and leading to elongated measuring times. Furthermore, white light sources generate a broad spectrum of spectral wavelengths, necessitating the use of expensive filters because a vast fraction of generated light of other wavelengths is not used in the application and needs to be blocked. In addition, white light sources produce heat which needs to be conducted away from the instrument.

Some instruments known in the art produce excitation beams by a single light-emitting diode (e.g., the Roche Lightcycler® 1.5 and 2.0) or by a laser (e.g., the ABI Prism 7700, 7900 as described in WO 2003/098278). Other instruments employ multiple light-emitting diodes of the same wavelength (e.g., the Eppendorf Mastercycler® realplex instrument described in WO 2003/002991). These instruments are necessarily limited to a single excitation wavelength. Consequently hydrolysis multiplex applications can not be performed without complex modifications in the instrument because the set of useful dyes is limited by the excitation wavelength.

Still other instruments such as the Cepheid Smartcycler (see U.S. Pat. No. 6,369,893), use several light-emitting diodes of different wavelengths for exciting the chemical reaction being tested. Several detectors are used for detection of the emitted light from the same reaction. This is disadvantageous if a plurality of reactions need to be analyzed because all the components of the instrument, such as LEDs and detectors, may need to be multiplied by the number of reactions to be analyzed. In addition, the number of filters and dichroic mirrors, as well as the electronic circuits for driving the LEDs and preamplify the signals of the photodiodes may also need to be increased. In addition, the complexity is still more increased when more than 4 LED types of distinct wavelengths are used. Therefore, when several reactions need to be detected with a detection system such as described in U.S. Pat. No. 6,369,893, the complexity and costs of the detection system become very high.

Also known in the art are spectrometer instruments, such as those disclosed in DE 4424961. Such instruments use a static light source and optical fibers, each fiber being connected on the one end to one sample area and on the other end to a rotary wheel. By turning the wheel each reaction region of the sample area may be brought into optical contact with the static light source. However, an instrument with this concept has the disadvantage that the light of the single light source is applied sequentially to each reaction region. It is not possible to detect several dye-markers with distinct excitation and emission spectra in several reaction regions in parallel with this instrument. This results in long measurement times, especially when a lot of samples need to be measured repeatedly, leading to long overall process times.

SUMMARY OF THE INVENTION

In one embodiment of the invention, there is provided an apparatus for emitting and detecting light, comprising at least two reaction regions located within the apparatus, an excitation module, the excitation module also being located within the apparatus and comprising at least two excitation light sources capable of providing light of distinct spectra, at least two first light guides, also being located within the apparatus, each first light guide being capable of directing light emitted from one of the excitation light sources to at least one of the reaction regions, at least two second light guides, also being located within the apparatus, each second light guide being capable of directing light emitted from one of the reaction regions to an emission module, an emission module, also being located within the apparatus, the emission module being capable of detecting beams emitted from each of the at least two reaction regions separately and simultaneously, the emission module at least comprising two detectors and a rotary filter wheel, the rotary filter wheel being positioned between the at least two second light guides and the detectors, and a control unit capable of controlling the activity of the excitation light sources and of the emission module, wherein the activity of the excitation light sources and the rotation of the rotary filter wheel of the emission module are electronically coupled; and wherein the rotary filter wheel is rotated in such a manner that for each reaction region, a filter on the rotary filter wheel having a transmission spectrum corresponding to the emission spectrum of light emitted from the reaction region when excited by excitation light is between the detector and the at least two second light guides when the reaction region is excited by the excitation light.

A second embodiment of the invention is an instrument for amplifying and detecting nucleic acids, comprising a device for subjecting a sample to amplification and/or nucleic acid hybrid melting reactions, and an apparatus for emitting and detecting light, comprising: at least two reaction regions located within the apparatus, an excitation module, the excitation module also being located within the apparatus and comprising at least two excitation light sources capable of providing light of distinct spectra, at least two first light guides, also being located within the apparatus, each first light guide being capable of directing light emitted from one of the excitation light sources to at least one of the reaction regions, at least two second light guides, also being located within the apparatus, each second light guide being capable of directing light emitted from one of the reaction regions to an emission module, an emission module, also being located within the apparatus, the emission module being capable of detecting beams emitted from each of the at least two reaction regions separately and simultaneously, the emission module at least comprising two detectors and a rotary filter wheel, the rotary filter wheel being positioned between the at least two second light guides and the detectors, and a control unit capable of controlling the activity of the excitation light sources and of the emission module, wherein the activity of the excitation light sources and the rotation of the rotary filter wheel of the emission module are electronically coupled; and wherein the rotary filter wheel is rotated in such a manner that for each reaction region, a filter on the rotary filter wheel having a transmission spectrum corresponding to the emission spectrum of light emitted from the reaction region when excited by excitation light is between the detector and the at least two second light guides when the reaction region is excited by the excitation light.

A third embodiment of the invention is a method for detecting specimens in a sample, comprising providing a sample in one of the at least two reaction regions of an apparatus, the sample comprising a plurality of detectable markers capable of generating light upon excitation by light of a wavelength different from that emitted, illuminating the sample with excitation light of distinct wavelength spectra emitted from at least two excitation light sources of the apparatus, and detecting the emission light emitted from the sample with an emission module of the apparatus, the apparatus comprising comprising at least two reaction regions located within the apparatus, an excitation module, the excitation module also being located within the apparatus and comprising at least two excitation light sources capable of providing light of distinct spectra, at least two first light guides, also being located within the apparatus, each first light guide being capable of directing light emitted from one of the excitation light sources to at least one of the reaction regions, at least two second light guides, also being located within the apparatus, each second light guide being capable of directing light emitted from one of the reaction regions to an emission module, an emission module, also being located within the apparatus, the emission module being capable of detecting beams emitted from each of the at least two reaction regions separately and simultaneously, the emission module at least comprising two detectors and a rotary filter wheel, the rotary filter wheel being positioned between the at least two second light guides and the detectors, and a control unit capable of controlling the activity of the excitation light sources and of the emission module, wherein the activity of the excitation light sources and the rotation of the rotary filter wheel of the emission module are electronically coupled; and wherein the rotary filter wheel is rotated in such a manner that for each reaction region, a filter on the rotary filter wheel having a transmission spectrum corresponding to the emission spectrum of light emitted from the reaction region when excited by excitation light is between the detector and the at least two second light guides when the reaction region is excited by the excitation light.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, where present, like reference numbers indicate identical or functionally similar elements.

light guides, the first light guide (31) routing the light emitted from one light source to one reaction region (1) and the $2^{nd}$ light guide (32) routing light emitted from the reaction region to the emission module (21).

Figure 4:
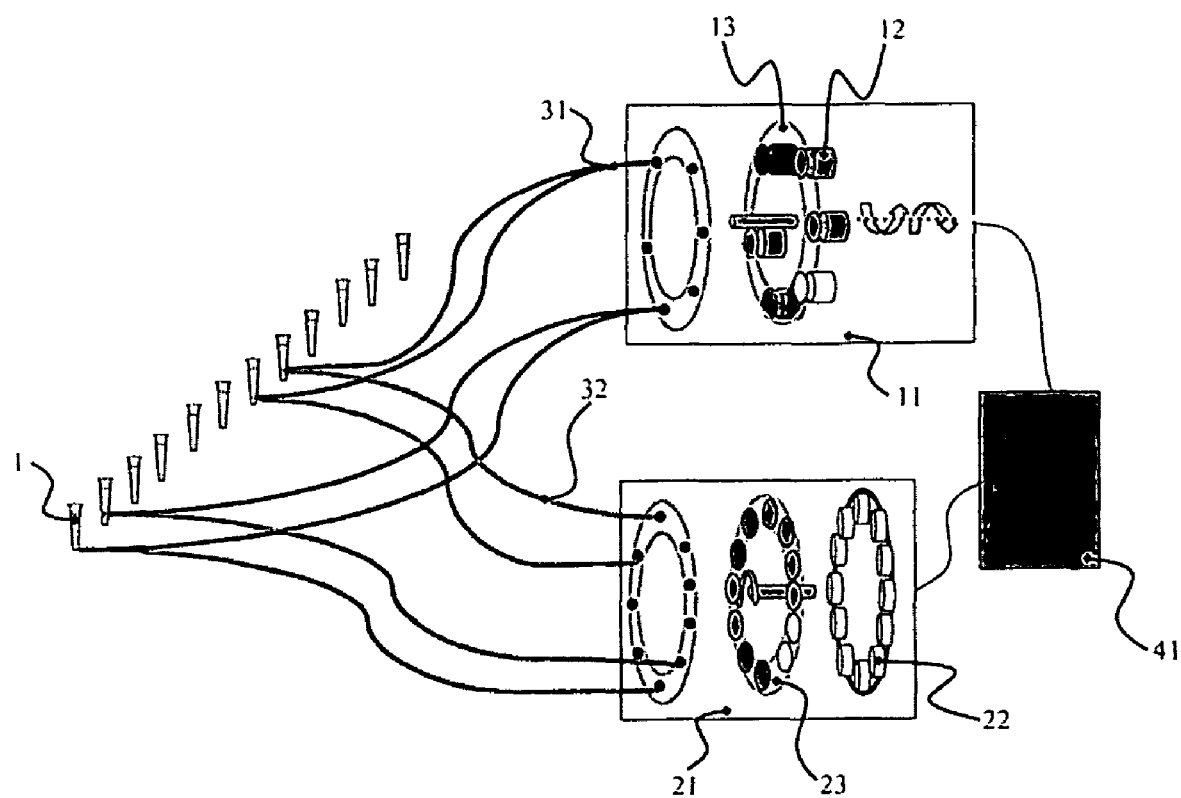

FIG. 4 shows another embodiment of the invention, wherein the apparatus for emitting and detecting beams of light comprises an excitation module (11) with light emitting diodes of various distinct wavelengths as the light sources (12) mounted on a rotary wheel (13) using bifurcated excitation fiber bundles as first light guides (31).

Figure 1:
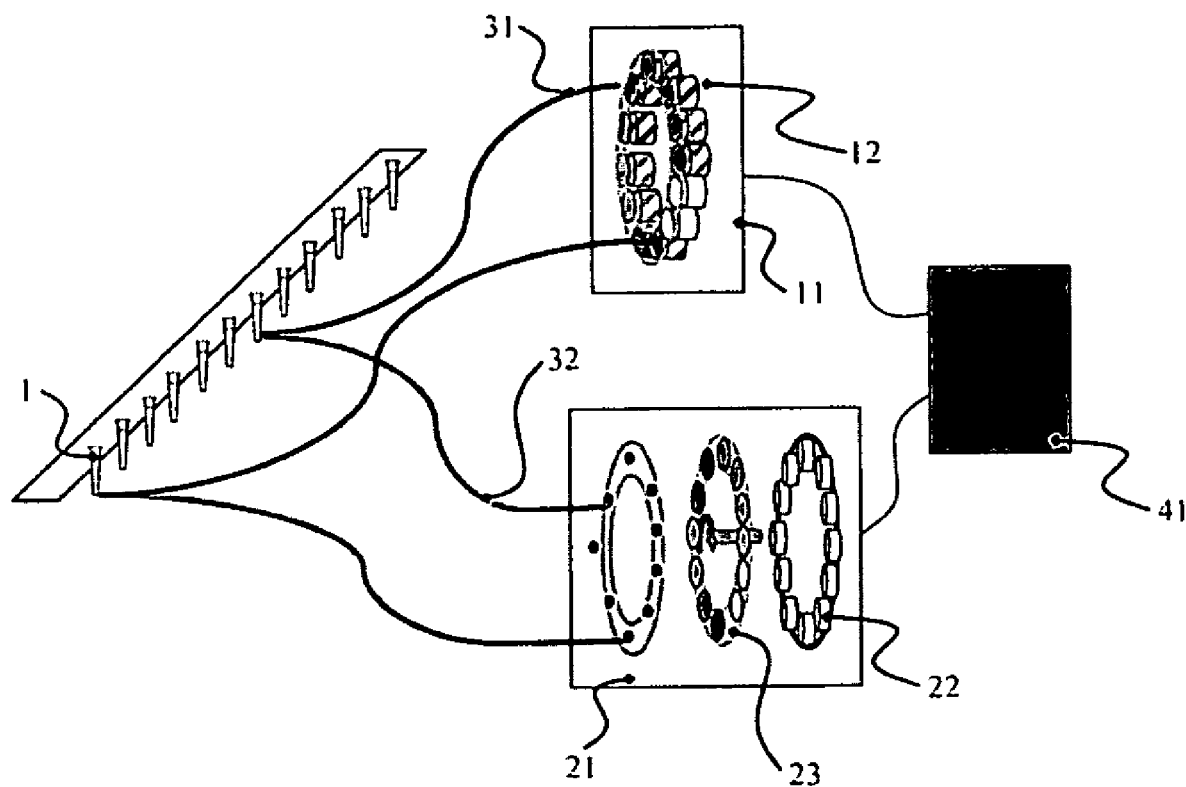
FIG. 1 shows one embodiment of the invention, specifically an apparatus for emitting and detecting beams of light comprising an excitation module (11) with multi-wavelength illuminators as the light sources (12), an emission module (21) comprising a rotary filter wheel (23) and detectors (22), a control unit (41), and first (31) and second (32) light guides, the first light guide (31) routing the light emitted from one light source to one reaction region, (1) and the $2^{nd}$ light guide (32) routing light emitted from the reaction region to the emission module (21).
Figure 3:
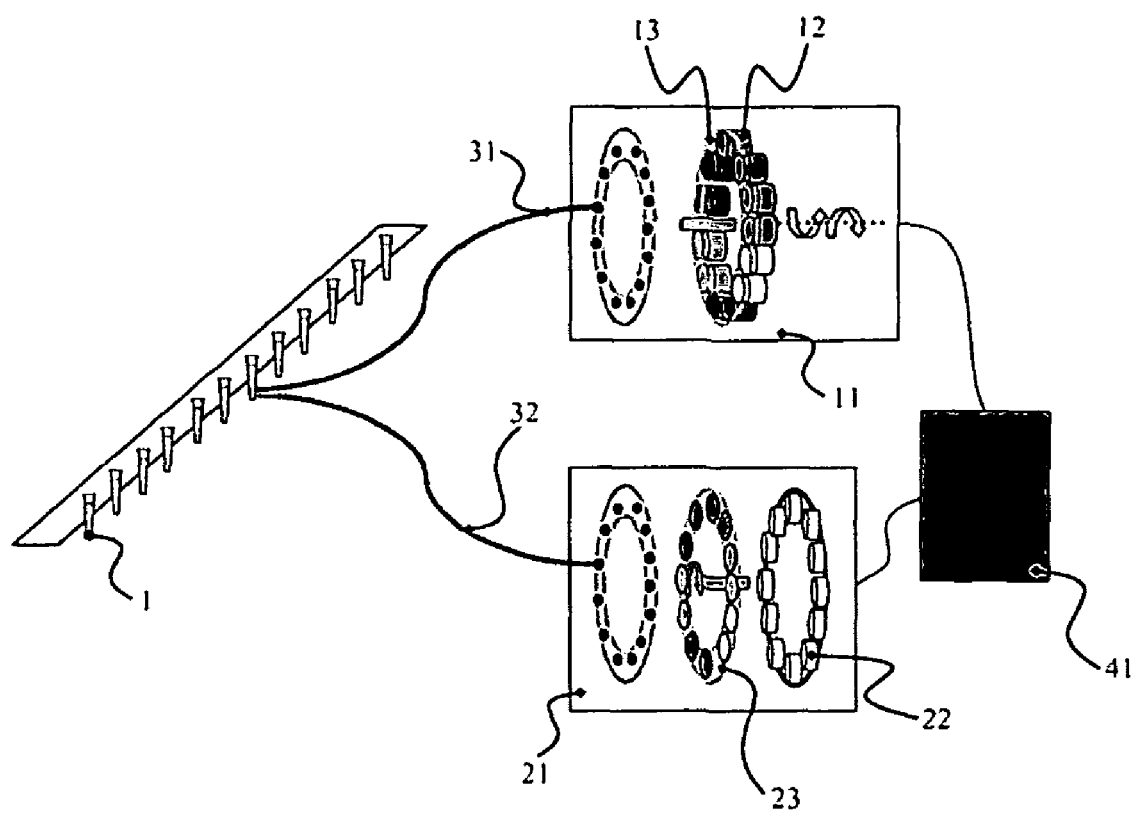
FIG. 3 displays another embodiment of the invention, wherein apparatus for emitting and detecting beams of light comprises an excitation module (11) with light emitting diodes (LEDs) of various distinct wavelengths as the light sources (12) mounted on a rotary wheel (13), an emission module (21) comprising a rotary filter wheel (23) and detectors (22), a control unit (41), and first (31) and second (32)
Figure 5:
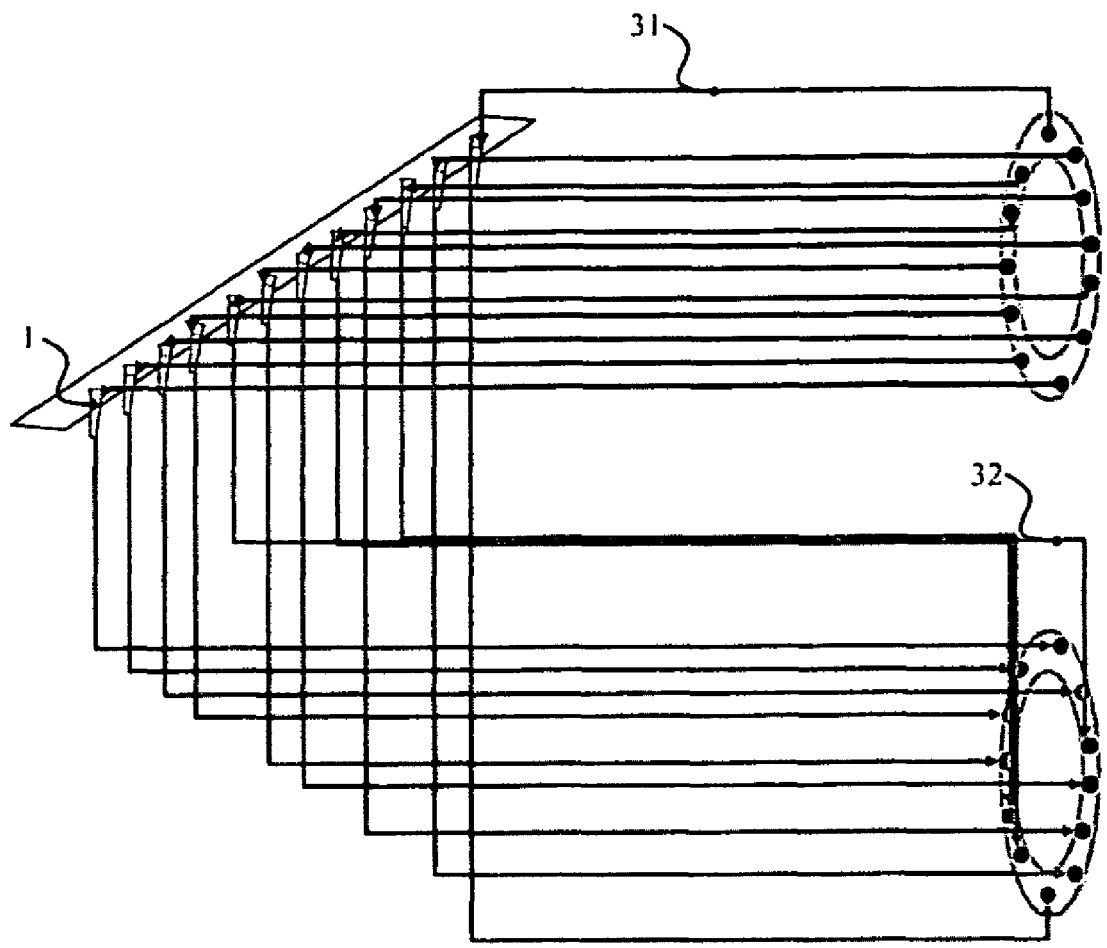

FIG. 5 is a schematic, showing the distribution of the first (31) and second (32) light guides in an embodiment of the invention as shown in FIGS. 1 and 3, each first light guide routing the light emitted from a light source (12) at a particular position to a particular reaction region (1) and each second light guide (32) routing the light emitted from a particular reaction region to a particular position within the emission module (21).

Figure 2:
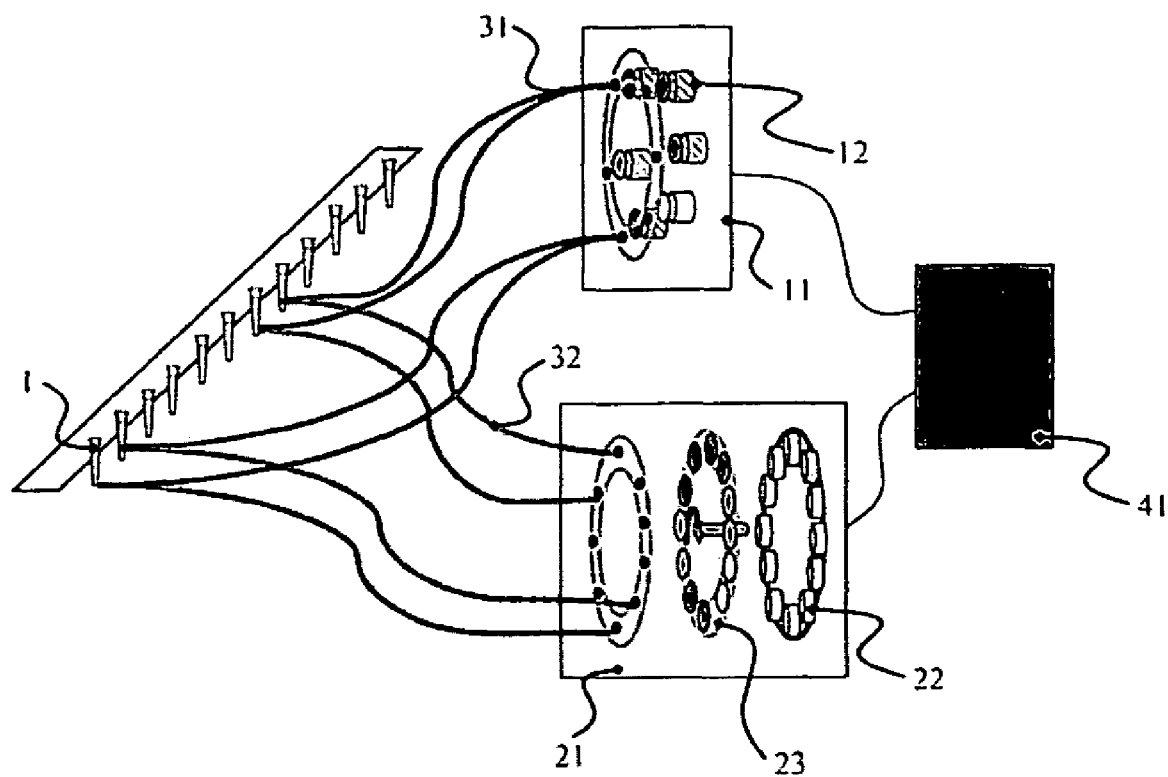
FIG. 2 shows another embodiment of the invention, wherein the apparatus for emitting and detecting beams of light comprises an excitation module (11) with multi-wavelength illuminators as the light sources (12) using bifurcated excitation fiber bundles as first light guides (31).
Figure 6:
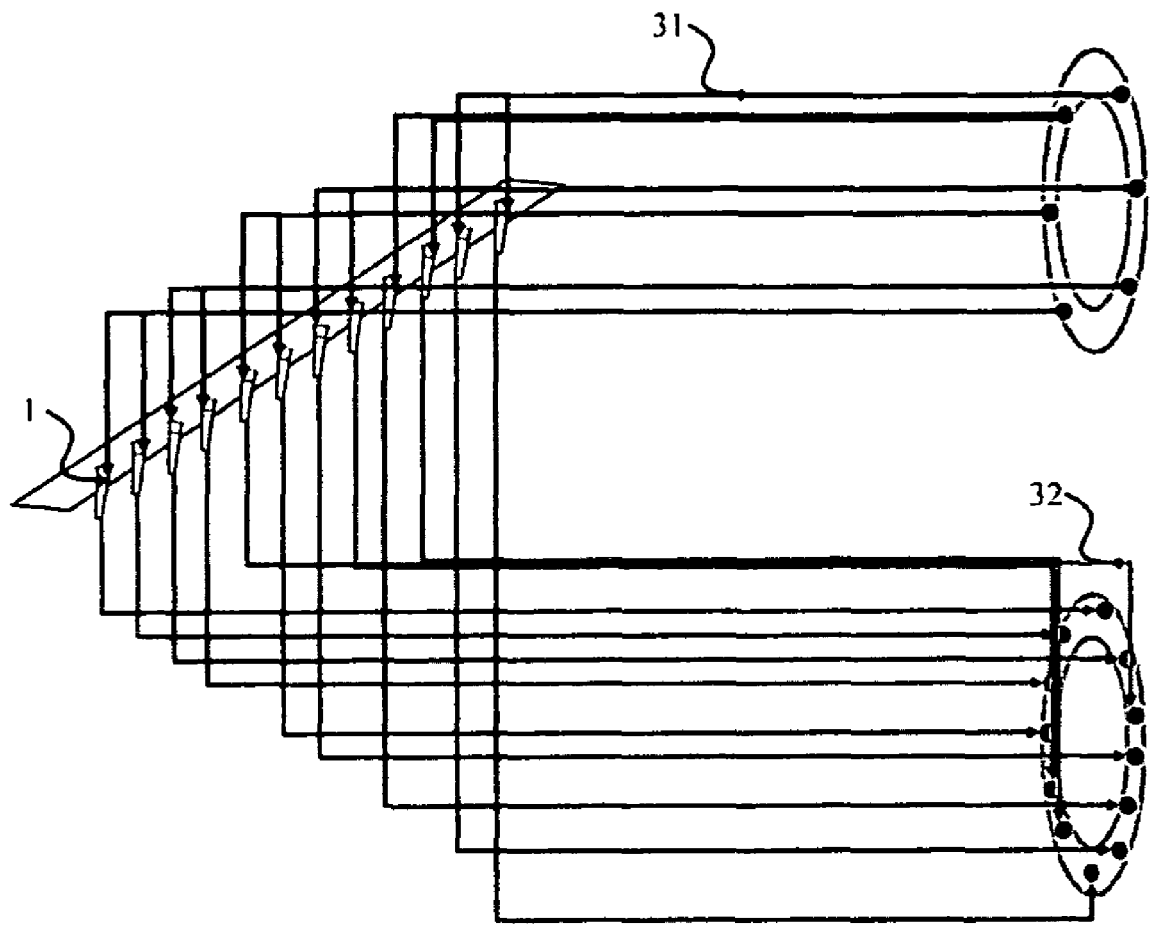

FIG. 6 is a schematic of the distribution of the first (31) and second (32) light guides in an embodiment of the invention as shown in FIGS. 2 and 4, each bifurcated first light guide routing the light emitted from a light source (12) at a particular position to two particular reaction regions (1) and each second light guide routing the light emitted from a particular reaction region to a particular position within the emission module (21).

Figure 7:
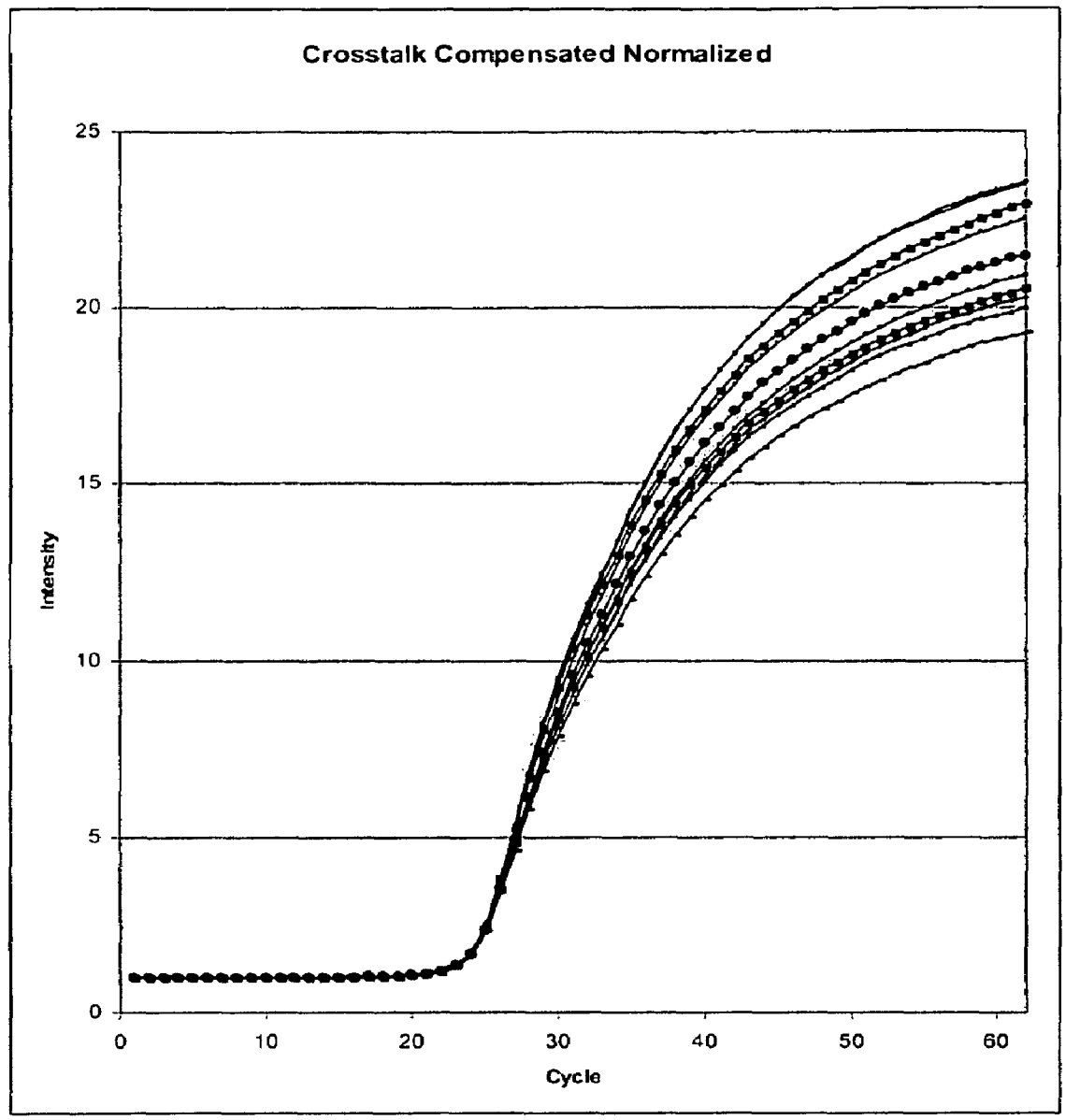

FIGS. 7 and 8 show amplification curves of the fluorescence intensity of a PCT run using an instrument according to the invention and a target template concentration of $10^6$ copies of HCV mRNA per μl and 40 copies of quantification standard (QS) per μl. The target probe was labeled with 6-carboxyfluorescein (FAM) dye while the QS probe was labeled with hexachlorofluorescein (HEX) dye. These two types of targets were amplified simultaneously by a multiplex PCR run. A total of 10 samples were processed. FIG. 7 shows the amplification curves of the target FAM-fluorescence intensity levels, FIG. 8 those of the QS HEX-fluorescence intensity levels.

FIG. 9 shows a sequence diagram of the different measurement steps which are required in order to measure all dye-markers in all reaction regions. The sequence diagram refers to an embodiment with 6 different colors of light emitting diodes. The sequence diagram applies to a total of twelve reaction sites which contain samples with 6 different dye markers in each of them.

The embodiments represented in the Figures are set forth to aid the understanding of the invention, but are not to be construed as limiting.

DETAILED DESCRIPTION OF THE INVENTION

The present invention relates to an apparatus for emitting and detecting light and an instrument for amplifying and detecting nucleic acids comprising such an apparatus. Herein, a 'light source' according to the invention may be a light-emitting diode (LED), an organic light-emitting diode, a laser (e.g., gas laser, chemical laser, excimer laser, solid state laser, semiconductor laser, dye laser, micro-wire laser) or a combination thereof.

A light-emitting diode (LED) is a semiconductor device that emits incoherent narrow-spectrum light (electroluminescence) when electrically biased in the forward direction. The color of the emitted light depends on the chemical composition of the semi-conducting material used and can be near-ultraviolet, visible or near-infrared. The wavelength of the light emitted, and therefore its color, depends on the band gap energy of the materials forming the p-n junction. In silicon or germanium diodes, the electrons and holes recombine by a non-radiative transition which produces no optical emission, because these are indirect band gap materials. If the emitting layer material of an LED is an organic compound, it is known as an Organic Light Emitting Diode (OLED). To function as a semiconductor, the organic emitting material must have conjugated pi bonds. The emitting material can be small organic molecules in a crystalline phase, or a polymer. Polymer materials can be flexible; such LEDs are known as PLEDs or FLEDs. Compared with regular LEDs, OLEDs are lighter and polymer LEDs can have the added benefit of being flexible. Recently, a new generation of LEDs (e.g. type Luxeon Star, Philips Lumiled) was developed, which have considerably more optical power than conventional LEDs. These LEDs may be used in optical systems if the optical power of conventional LEDs is not sufficient for measuring various samples with sufficient sensitivity. Furthermore, these high-power LEDs are just a little bigger than conventional LEDs. Thus, only small cooling blocks are required because the emitted heat is considerably smaller than with conventional white light sources.

Furthermore, LEDs called 'multi-wavelength illuminator' are known in the art. Herein, one device provides multiple LED chips packaged into a compact, thermally conductive ceramic substrate having individually controlled multiple wavelengths that range from ultra-violet through the visible red spectrum.

The use of LEDs is advantageous as LEDs are durable and are extremely long-lived with a life-span of 100,000 operating hours or more. Another advantage is that LEDs are very small in comparison to traditional white light sources. Therefore, several LEDs may be placed in an "excitation module" or may be mounted on a rotary wheel in an "excitation module". The excitation module may also contain cooling blocks and the accompanying optics such as lenses and filters, either together or separately.

A "light source" may also be a laser that emits photons in a coherent beam. A laser commonly contains an active laser medium or gain medium capable of generating stimulated emission on electronic or molecular transitions to a lower energy state starting from a higher energy state to which it had been previously stimulated by energy transfer from an external source. Various materials have been found to possess the required characteristics to form the laser gain medium needed to power a laser (gas, liquids, dyes, solid materials). Thus, many types of lasers with different characteristics suitable for different applications have been developed. The advantage for the use of lasers in an apparatus according to the invention is that laser light typically is emitted in a narrow beam and is near-monochromatic and consists of a single wavelength or color. Furthermore, lasers may be used in applications where many samples are excited with one color in parallel as lasers provide light of high power.

The "excitation module" refers to a part of the apparatus containing one or more of the "light sources" which emit light in order to excite particular dyes in a sample placed in the reaction regions. In certain embodiments the "excitation module" of the apparatus further comprises a "rotary wheel" which contains or carries the light sources for excitation of the reaction regions. Furthermore, in certain embodiments filters of appropriate center wavelengths and bandwidths may be mounted on the rotary wheel along with lenses which may be necessary to collimate the light from the light sources.

The "emission module" refers to a part of the apparatus containing at least two detectors which detect light emitted from the samples in the reaction regions. A "detector" is a component which converts light into an electrical current proportional to the incident light (photons). The "emission module" may further comprise a "rotary filter wheel" which contains filters that filter the light emitted from the samples in the reaction regions. Filters are needed in order to block and/or separate light emitted by the light sources from the light emitted by the dyes within the samples, because the light from the light sources may be scattered in the reaction regions and in other components of the optical system. Lenses may be present in the emission module in order to collimate the light through the filters.

A "light guide" is used for transporting or distributing natural or artificial light. A "light guide" may also be an optical fiber made up of glass or plastic and designed to guide light along its length by total internal reflection. Such optical fibers are widely used in fiberoptic communication. A "light guide" may on the one hand be a single glass or plastic fiber or on the other hand may consist of such fibers. Another example for a "light guide" is a glass or a plastic rod. Another type of "light guide" is a fluid light guide. All these types of "light guides" can either be bifurcated or not bifurcated. Furthermore, bifurcated "light guides" may either be dually or multiply branched.

As used herein the term "reaction region" refers to an area or section within the apparatus of the invention that is capable of holding a sample containing dyes to be measured. In certain embodiments a "reaction region" refers to a vessel which is placed at a particular position within the apparatus and which contains a sample comprising dyes which are measured by the apparatus.

The "control unit" contains the controller which controls the movement of various movable portions of the apparatus, such as the rotary filter wheel. The "control unit" may also control the operation of the light sources and/or the detectors. In some In some embodiments, the "control unit" coordinates the rotation of the rotary filter wheel and the operation of light sources and detectors. In certain embodiments, the "control unit" further controls the movement of the rotary wheel carrying the light sources and coordinates the movement of the rotary wheel and the operation of the light sources with the movement of the rotary filter wheel and the operation of the detectors.

In one embodiment of the invention the apparatus for emitting and detecting beams of light comprises at least two reaction regions, and an excitation module comprising at least two excitation light sources capable of providing excitation beams of distinct spectra and wavelengths. It further may comprise at least two first light guides, each first light guide being capable of directing light emitted from one of the excitation light sources to at least one of the reaction regions and at least two second light guides, each second light guide being capable of directing light emitted from one of the reaction regions to an emission module. The apparatus further may comprise an emission module capable of detecting light emitted from each of the at least two reaction regions separately and simultaneously. The emission module at least comprises two detectors and a rotary filter wheel, wherein the filter wheel is positioned between the at least two second light guides and the detectors. Furthermore, the apparatus may comprise a control unit capable of controlling the excitation module (i.e., the activation of the light sources mounted thereon) and the emission module (i.e., the rotation of the rotary filter wheel). Herein the activity of the excitation light sources and the rotation of the rotary filter wheel of the emission module are electronically coupled. The rotary filter wheel is rotated in such a manner that for each reaction region the transmission spectrum of the filter mounted on the rotary filter wheel corresponds to the emission spectrum of the light emitted from the reaction region when the reaction region is excited by excitation light. By "corresponds" it is meant that the transmission spectrum of the filter aligns or overlaps with that of the emission spectrum to a degree that a usable or detectable portion of the emitted light from the reaction region passes through the filter. Moreover, the excitation light sources are capable of providing excitation light of various distinct spectra and wavelength. Such excitation light sources may be LEDs, laser diodes or any other light sources with distinctive color. Such an apparatus allows a first excitation light source of said at least two excitation light sources that emits light of a first wavelength which is transmitted via a first light guide to at least a first reaction region and a second excitation light source of said at least two excitation light sources which simultaneously emits light of a second wavelength different from said first wavelength which is transmitted via a second light guide to at least a second reaction region. This enables the parallel excitation and measurement of at least two reaction regions with different wavelengths in one measurement step. This is advantageous as particular measurement sequences may be performed in a fast and efficient manner, allowing in a first step the simultaneous measurement of at least two reaction regions excited with beams of light of a different wavelength and in a successive second step allowing the simultaneous measurement of at least two reaction regions excited with beams of light of different wavelength, e.g. inversely to the wavelengths used in the first step, by altering the excitation wavelengths of the light sources within the excitation module and the concurrent rotation of the rotary filter wheel in the emission module. In applications such as multiplex PCR more than one dye marker is present in each sample. Using such a sequence of measurement steps therefore leads to a much shorter overall sequence measurement time compared to successive applications of measurement steps of just one dye-specific excitation and measurement wavelength. An exemplary embodiment of such a measurement sequence is described below for FIG. 9.

Another advantage of the present invention is that by guiding the emitted optical power from one particular light source to just one or a few reaction regions the optical power at each reaction region is high. This enables shortening each particular measurement step, which leads to a short sequence measurement time.

In certain embodiments LEDs are used as the "light source". This is advantageous as LEDs are comparatively inexpensive, and in general have long life times leading to reduced maintenance costs. In certain aspects, multi-wavelength illuminators capable of providing several wavelengths are used.

Fluorescent dyes or dye markers may include dyes that are negatively charged, such as dyes of the fluorescein family, or dyes that are neutral in charge, such as dyes of the rhodamine family, or dyes that are positively charged, such as dyes of the cyanine family. Dyes of the fluorescein family include, e.g., FAM, HEX, TET, JOE, NAN and ZOE. Dyes of the rhodamine family include Texas Red, ROX, R110, R6G, and TAMRA. Various dyes or nucleotides labeled with FAM, HEX, TET, JOE, NAN, ZOE, ROX, R110, R6G, Texas Red and TAMRA are marketed by Perkin-Elmer (Boston, Mass.), Applied Biosystems (Foster City, Calif.), or Invitrogen/Molecular Probes (Eugene, Oreg.). Dyes of the cyanine family include Cy2, Cy3, Cy5, and Cy7 and are marketed by GE Healthcare UK Limited (Amersham Place, Little Chalfont, Buckinghamshire, England).

In a particular embodiment the first light guide may be bifurcated. In such an embodiment more than one reaction region may be excited at the same time by one particular light source. Such an embodiment provides an even higher throughput of samples to be measured.

In another embodiment, one end of each of at least two first light guides is affixed to a particular position on an excitation module allowing optical contact of one excitation light source with a first light guide. The other end of each of the at least two first light guides is affixed to at least one reaction region, thereby leading the beam of light emitted from the excitation light source to a defined position at the reaction region. Each of at least two light guides is locally fixed in a particular position within the apparatus in such a way that one particular first light guide guides the light from one particular position next to one light source (e.g., a multi-wavelength illuminator) to one particular reaction region and that one particular second light guide guides the light emitted from this reaction region to one particular position next to the rotary filter wheel. Instead of one light source, multiple light sources of the same wavelength may be present at a particular position on the excitation module in order to increase the intensity of light. Alternatively, light emitted from multiple light sources of the same wavelength may be conveyed to a particular position on the excitation module using a third light guide or a bundle of third light guides. By emitting light of desired wavelengths from the light one or more sources and by rotating the rotary filter wheel in a coordinated manner, one sample in one reaction region containing several dyes may be excited with light of different wavelengths correlating to the excitation spectra of the various dyes in a short period of time. As each excitation beam acts on the sample, the emission spectrum of the sample for each excitation beam can be measured simultaneously.

In certain aspects the excitation light sources are switched off by the control unit while the rotary wheel rotates. This is advantageous because it allows recording a dark value and correcting the measured signals emitted from the reaction regions. Besides the signal from the dye components, the measured signal may contain a dark value that is caused by offset of the signal processing electronics. Furthermore, switching off the light sources is advantageous with certain types of light sources, such as LEDs, as it reduces the spectral changes of the emitted light. Spectral changes of the light emitted from LEDs may affect the measurement because of the higher warm-up of the LEDs or semiconductor laser diodes during continuous operation.

In certain embodiments each of at least two excitation light sources are capable of providing excitation light of various distinct spectra and wavelength. Two exemplary embodiments of such an apparatus are shown in FIGS. 1 and 2. Herein, the apparatus comprises excitation module (11) comprising multi-wavelength illuminators as the light sources (12), an emission module (21) comprising a rotary filter wheel (23) and detectors (22), a control unit (41), and first (31) and second (32) light guides for routing the light emitted from one light source (12) to one reaction region (1) and light emitted from this reaction region to the emission module (21), respectively. In the exemplary embodiment in FIG. 2 the apparatus comprises an excitation module (11) with multi-wavelength illuminators as the light sources (12) using bifurcated excitation fiber bundles as first light guides (31).

FIG. 1 shows an embodiment of the invention having fixed multi-wavelength illuminators as light sources (12) and not bifurcated first light guides (31) as well as twelve reactions regions (1). The light sources (12) are contained in the excitation module (11). All twelve light sources (12) are of the same type and each of these multi-wavelength illuminator light sources may provide six distinct wavelengths which may sequentially be switched on and off. In one embodiment, the activation of the multi wavelength illuminators is controlled in such a manner that always pairs of two adjacent multi-wavelength illuminators (12) emit light of the same color and wavelength. During each measurement step within a measuring sequence all light sources (12) are switched on in such a way that the six multi-wavelength illuminator pairs have distinct colors. Thereby, always two reaction regions (1) are illuminated with light of the same wavelength and up to six different wavelengths may be used in parallel in each measurement step. By applying to each reaction region (1) a measurement sequence of six consecutive measurement steps, wherein the color and wavelength of the excitation beam is altered for each measurement step, every reaction region (1) may be excited with light of six different wavelengths in a fast and efficient manner. The excitation light beams are guided from each of the multi-wavelength illuminators (12) to one of the reaction regions (1) by a first light guide (31). The emission beams from each of the twelve reaction regions (1) are guided to the emission module (21) by twelve second light guides (32). In FIG. 1 only two exemplary first light guides and two exemplary second light guides for two reaction regions are shown, whereas FIG. 5 displays a detailed schematic view of the arrangement of the first (31) and second light guides (32) showing all light guides. In the emission module (21) each emission beam from one reaction region (1) is led to one of the twelve detectors (22). Each emission beam is led through one filter which is mounted on a rotary filter wheel (23). The filters on this rotary filter wheel are selected and assembled in such a manner that the center wavelengths correspond to the spectra of the respective emission beams, that is, the center wavelength of the filters are at or near a $\lambda$ which is an emission peak or maximum of the emitted light. In this particular embodiment, filters of the same type are arranged pair wise and are mounted adjacent to each other on the rotary filter wheel (23). However, the arrangement of the filters on the rotary filter wheel (23) may depends on the arrangement of the first (31) and second light guides (32) with respect to the reaction regions (1) and may be adapted as suitable. Within a measurement sequence it may be necessary that each pair of multi-wavelength illuminators (12) sequentially emits light of all suitable wavelengths to be measured. The rotary filter wheel (23) is rotated at the end of each measurement step within the measurement sequence in such a way that the filters are positioned to provide the appropriate spectral characteristics to detect the emission spectra of the dye-markers excited by the appropriate excitation light. The change of the wavelengths of the excitation light beam emitted from the multi-wavelength illuminators (12) and the rotation of the rotary filter wheel (23) are coordinated by a control unit (41).

FIG. 2 shows another embodiment of the invention. In contrast to the embodiment of FIG. 1, the number of multi-wavelength illuminators (12) is reduced from twelve to six. The first light guides (31) are bifurcated to enable two reaction regions (1) to be illuminated with excitation light of the same spectra from the same single multi-wavelength illuminator. In FIG. 2 only two exemplary bifurcated first light guides having two branches and four exemplary second tight guides for four reaction regions are shown, whereas FIG. 6 displays a detailed schematic view of the arrangement of the first (31) and second light guides (32) showing all light guides.

In further embodiments the first light guides (31) may be divided into three or more branches in order to increase the number of reaction regions (1) which are illuminated by excitation light of the same spectra from the same single multi-wavelength illuminator (12) at a time. Moreover, in most applications it is reasonable to correlate the number of detectors (22) in the emission module (21) to the number of reaction regions (1) which need to be analyzed in order to allow for a defined measurement signal allocation as well as a fast and parallel measurement of all reaction regions. The filters on the rotary filter wheel need to be selected considering their spectral characteristics in such a manner that the number of filters with the same spectral specifications correlates to the number of reaction regions which are excited by excitation light of the same spectra.

A measurement sequence diagram for the measurement of all reaction regions as described above is depicted in FIG. 9. It shows the measurement sequence of an apparatus embodiment of the invention having twelve reaction regions and six or twelve multi-wavelength illuminators respectively. The necessary measurement steps within a measurement sequence required to analyze all samples in the reaction regions using six different dye-markers in each reaction region are displayed. A channel in this sequence diagram refers to a specific set of filters which allows measurement of one particular dye-marker present in the twelve reaction regions. In an embodiment having six multi-wavelength illuminators a channel encompasses one excitation filter and two emission filters of corresponding spectral characteristics. In an embodiment having twelve multi-wavelength illuminators two excitation filters for one channel may be used. The excitation filters may be positioned after the collimation lenses on the rotary wheel. In both embodiments channel 1 may be applied to the first and second reaction regions when measurement step 1 or a six-step measuring sequence is performed. At the same time the other channels 2-6, appropriately equipped for measuring the other types of dye-markers present in the samples, are applied to the remaining reaction regions 3-12. This is advantageous because suitable dye-markers in reaction regions 3-12 can measured in parallel to that in the reaction regions 1 and 2. Before the initiation of measurement step 2, all multi-wavelength illuminators switch their colors and wavelengths of the light emitted and the rotary filter wheel is rotated in such a way that channel 1 now is applied to the samples in the reaction regions 3 and 4. Thus, in measurement step 2 the same type of dye-marker as measured in reaction regions 1 and 2 during measurement step 1 is now being measured in reaction regions 3 and 4. At the same time all other channels 2-6 are positioned towards a new pair of reaction regions allowing the measurement of another type of suitable dye-marker present in the reaction regions. After applying all six measurement steps to all samples the six dye-markers in the twelve reaction regions have been measured with all six channels. Therefore, using this measurement sequence with an apparatus according to the invention is particularly useful in multiplex PCR, applications resulting in short sample measuring times of many samples with high sensitivity.

In other embodiments the number of reaction regions, excitation light sources, and excitation wavelengths may vary. There is also no necessity that the number of reaction regions needs to be a multiple of the number of dye-markers to be measured or a multiple of the number of different multi-wavelength illuminator colors. Furthermore, neither the number of multi-wavelength illuminators which emit the same color at a time nor the number of filter types having the same spectral characteristics are restricted.

In another embodiment of the invention an apparatus for emitting and detecting light comprises at least two reaction regions and an excitation module comprising at least two excitation light sources mounted on a rotary wheel, wherein the excitation light sources are capable of providing excitation light of distinct spectra. It further comprises at least two first light guides, each first light guide being capable of directing light emitted from one of the excitation light sources to at least one of the reaction regions and at least two second light guides, each second light guide being capable of directing light emitted from one of the reaction regions to an emission module. The apparatus further comprises an emission module capable of detecting light emitted from each of the at least two reaction regions separately and simultaneously. The emission module at least comprises two detectors and a rotary filter wheel, wherein the filter wheel is positioned between the at least two second light guides and the detectors. Furthermore, the apparatus comprises a control unit capable of controlling the excitation module (i.e., the rotation of the rotary wheel to a predetermined position and the activation of the light sources mounted thereon) and the emission module (i.e., the rotation of the rotary filter wheel). Herein, the rotary wheel carrying the excitation light sources may be rotated relative to the position of the at least one first light guide, allowing one of the excitation light sources to emit light to a defined first light guide. Moreover, the rotation of the rotary wheel carrying the light sources, the activity of the excitation light sources and the rotation of the filter wheel of the emission module are coupled electronically via the controller within the control unit, allowing the rotary filter wheel to be rotated in such a manner that for each reaction region the transmission spectrum of the filter mounted on the filter wheel corresponds to the emission spectrum of the light emitted from the respective reaction region. Thus, the rotary wheel carrying the excitation light sources may be rotated relative to the position of the first light guide, at least allowing one of the excitation light sources to emit light to one defined first light guide. The rotation of the rotary wheel to a predetermined position may be controlled by the control unit. Such an apparatus permits at least two processes to occur simultaneously—first a first excitation light source sources mounted on the rotary wheel emits light of a first wavelength which is transmitted via a first light guide to at least a first reaction region, and second a second excitation light source mounted on the rotary wheel emits light of a second wavelength different from said first wavelength which is transmitted via a second light guide to at least a second reaction region. This enables the parallel excitation and measurement at least two reaction regions with different wavelengths in one measurement step. This is advantageous as particular sequences of measurement steps may be performed in a fast and efficient manner, by allowing in a first step the simultaneous measurement of at least two reaction regions excited with light of the a different wavelength and in a successive second step allowing the simultaneous measurement of at least two reaction regions excited with light of different wavelength e.g. inversely to the wavelengths used in the first step by the coupled rotation of said rotary wheel carrying the light sources and the concurrent rotation of the rotary filter wheel in the emission module. An exemplary embodiment of such a measurement sequence is described below for FIG. 9.

In a certain embodiment the first light guide may be bifurcated or a light guide bundle may be used. In such an embodiment more than one reaction region may be excited at the same time by one light source mounted on the rotary wheel. Such an embodiment provides an even higher throughput of samples to be measured.

In certain aspect LEDs are used as the "light source" in the apparatus according to the invention. This is advantageous as LEDs are comparatively inexpensive and in general have long life times leading to low maintenance costs. Furthermore, the use of LEDs places less demand on the blocking requirements of the filters to be used because only smaller spectral ranges require high blocking which leads to much less expensive filters. Furthermore, a rotary wheel carrying LEDs consumes less space and allows the construction of more compact analytical instruments.

In certain embodiments each of at least two first light guides is at one end affixed to a particular position on an excitation module, allowing optical contact of one excitation light source with one first light guide and on the other end each of at least one first light guide is affixed to at least one reaction region mediating the light emitted from said excitation light source to a defined position at least one reaction region.

In certain aspects the excitation light sources are switched off by the control unit while the rotary wheel rotates. This is advantageous because it allows recording a dark value and correcting the measured signals emitted from the reaction regions which besides the signal contain the dark value that is caused by the offset of the signal processing electronics. Furthermore, switching off the light sources is advantageous as it reduces the amount of heat emitted by the light sources and, thus, decreases the risk that the spectral changes of the light sources caused by their higher inside temperatures have an undesired impact on the accuracy of the measurements.

In certain embodiments the excitation light sources each represent different excitation wavelengths. In other embodiments the apparatus according to the invention comprises light sources of different colors with several light sources of the same color being present at each particular position on the rotary wheel in such a manner that at each position on the rotary wheel several light sources of the same color conjointly form one light source. Herein, at each particular light source position on the rotary wheel the light emitted by multiple light sources of the same color can be guided to the reaction regions by bifurcated or unbifurcated light guides. The advantage of this embodiment is that it provides higher optical power to the reaction regions, which is especially advantageous when a lot of reaction regions are present.

During one measurement step light of a defined wavelength is emitted from one excitation light source mounted on a rotary wheel and is guided to a reaction region via a first light guide. Within the reaction region the light may interact with at least one dye contained in a sample leading to the emission of light from the reaction region. The emitted light is guided to a filter mounted on the rotary filter wheel of the emission module via a second light guide. The transmissibility of the filter is chosen to correlate to the wavelength of the light emitted from the reaction region. Light that has passed through the filter wheel is then detected by a detector of the emission module. The signal of the detector is then evaluated and may be edited. The first and the second light guides are locally fixed in a particular position within the apparatus in such a way, that one particular first light guide guides the light from one particular position next to the rotary wheel carrying the light sources to one particular reaction region and that one particular second light guide guides the light emitted from this reaction region to one particular position next to the rotary filter wheel. By rotating the rotary wheel carrying the light sources and by rotating the rotary filter wheel in a coordinated manner one sample in one reaction region containing several dyes may be excited with light of different wavelengths correlating to the excitation spectra of the various dyes in a short period of time, while during each excitation of the sample the emission spectrum of the sample for this excitation can be measured simultaneously. In principal every position of the rotary wheel carrying the light sources may be correlated to a user-defined position of the rotary filter wheel leading to a high flexibility of combining excitation and emission wavelengths. Thus, with a limited amount of coordinated rotary movements of the two rotary wheels one sample can be excited with light of different wavelengths in a short period of time, which is advantageous particularly when evaluating a sample in a multiplex PCR assay. Thus, it becomes possible to illuminate all samples provided in various reaction regions with light of different wavelengths by just a few rotations. Because of the arrangement of the different light sources on the rotary wheel the different samples are illuminated by different colors during each single measurement step. This illumination pattern is changed at the next following measurement step of a measurement sequence in this way that at the end of the sequence all samples were combined with all colors. The total time of a measurement sequence is minimized because of the parallelization of many measurements at every measurement time point.

Two exemplary embodiments of such embodiments of the apparatus are depicted in FIGS. 3 and 4. FIG. 3 shows a certain embodiment of the invention having twelve LEDs as light sources (12) mounted on a rotary wheel (13), twelve reaction regions (1) and not bifurcated first light guides (31). The LEDs (12) mounted on the rotary wheel (13) are contained in the excitation module (11). In this particular embodiment each two adjacent LEDs (12) of the twelve LEDs mounted on the rotary wheel (13) pairwise have distinct colors. The excitation light beams are guided from the LEDs (12) to the reaction regions (1) by first light guides (31). In this setup each two reaction regions are illuminated with the same color. As the position of the light guides (31) within the excitation module (11) is fixed, every reaction region (1) can be brought into optical contact with every light source by rotating the rotary wheel (13) to a predetermined position. At the beginning of each measurement step within a measuring sequence all LEDs are switched on. Thereby, always two reaction regions are illuminated with light of the same wavelength and up to six different wavelengths may be used in parallel in each measurement step. After each measurement step the rotary wheel (13) carrying the LEDs (12) is rotated by two positions in order to allow the LEDs that were in optical contact with the first light guides (31) leading to reaction regions 1 and 2 in measurement step 1 to be in optical contact with the first light guides leading to reaction regions 3 and 4 in measurement step 2 and so forth. By applying a measurement sequence of six measurement steps, wherein the color and wavelength of the excitation beam is altered for each measurement step by rotating the rotary wheel (13) carrying the LEDs accordingly, every reaction region (1) may be excited with light of six different wavelengths in a fast and efficient way. The emission light emitted from the twelve reaction regions (1) is guided to the emission module (21) by twelve second light guides (32). In FIG. 3 only one exemplary first (31) and second light guide (32) for one reaction region is depicted, whereas FIG. 5 displays a detailed schematic view of the arrangement of the first (31) and second light guides (32) showing all light guides. In the emission module (21) each emission beam is led to one of the twelve detectors (22) by a second light guide (32). Hereby, each emission beam is led through one filter which is mounted on a rotary filter wheel (23). The filters on this rotary filter wheel are selected and assembled in such a manner that their spectral characteristics fit to the spectra of the respective emission light. In this particular embodiment filters of the same type regarding the spectral specifications are arranged pairwise and are mounted adjacent to each other on the rotary filter wheel (23). However, the arrangement of the filters on the rotary filter wheel (23) depends on the arrangement of the first

(31) and second light guides (32) with respect to the reaction regions (1) and may be adapted as suitable. The color pattern of the six LED pairs and the filters on the rotary filter wheel (23) should be selected in such a way that all pairs of reaction regions (1) are illuminated by excitation beams of distinct spectra. Before the beginning of each measurement step within a measurement sequence each pair of LEDs is guided to the ends of the first light guides (31) fixed in the excitation module (11) by rotation of the rotary wheel (13). Thereby, within one measurement step all pairs of reaction regions (1) are illuminated with distinct excitation beams. In parallel the rotary filter wheel (23) is rotated at the beginning of each measurement step in such a way that the filters are positioned to provide the appropriate spectral specifications in order to detect the emission spectra of the dye-markers excited by the appropriate excitation light. After measurement at the end of the measurement step and before the initiation of the next measurement step the rotary wheel (13) carrying the light sources (12) and the rotary filter wheel (23) are rotated to the next measurement position. The rotation of the rotary wheel (13) and the rotation of the filter rotary wheel (23) in a coordinated manner are controlled by a control unit (41).

FIG. 4 shows another embodiment of the invention. In contrast to the embodiment of FIG. 3 the number of LEDs (12) is reduced to six instead of twelve, wherein these six LEDs have distinct colors. The first light guides (31) are bifurcated with two branches in order to enable that two reaction regions (1) are illuminated with excitation light of the same spectra from the same single LED (12). In FIG. 4 only two exemplary bifurcated first light guides (31) having two branches and four exemplary second light guides (32) for four reaction regions are shown, whereas FIG. 6 displays a detailed schematic view of the arrangement of the first (31) and second light guides (32) showing all light guides. In further embodiments the first light guides may be bifurcated having more than two branches in order to increase the number of reaction regions (1) which are illuminated by excitation beams of the same spectra from the same LED at a time. Moreover, in most applications it is reasonable to correlate the number of detectors (22) in the emission module (21) to the number of reaction regions (1) which need to be analyzed in order to allow for a defined measurement signal allocation as well as a fast and parallel measurement of all reaction regions. The filters on the rotary filter wheel (23) need to be selected regarding their spectral specifications in such a manner that the number of filters with the same spectral specifications correlates to the number of reaction regions (1) which are excited by excitation light of the same spectra.

The measurement sequence diagram for the measurement of twelve reaction regions and each reaction region comprising a sample containing six different dye-markers as described above and as depicted in FIG. 9 may also be applied to embodiments as displayed in FIGS. 3 and 4. In each measurement step all six LEDs or six pairs of LEDs with the same color are guided to the next adjacent pair of first light guide ends in the excitation module by rotation of the rotary wheel. In parallel the rotary filter wheel is rotated in the same manner accordingly. This ensures that the channel in optical contact with reaction regions 1 and 2 in a first measurement step is applied to the samples in the reaction regions 3 and 4 in the next measurement step. Thus, in this measurement step the same dye-marker as measured in the previous measurement step in reaction regions 1 and 2 may now be measured in reaction regions 3 and 4. At the same time all other channels 2-6 are in position to a new pair of reaction regions in comparison to the previous measurement step allowing the measurement of another type of suitable dye-marker present in the reaction regions. After applying all six measurement steps to all samples the six dye-markers in the twelve reaction regions were measured with all six channels. Therefore, using this measurement sequence with an apparatus according to the invention is particularly useful in multiplex PCR applications permitting short sample measuring times of many samples combined with high sensitivity.

In other embodiments the number of reaction regions, excitation light sources, and excitation wavelengths may vary. There is also no necessity that the number of reaction regions needs to be a multiple of the number of dye-markers to be measured or a multiple of the number of different light source colors respectively. Furthermore, neither the number of light sources which emit the same color at a time nor the number of filter types having the same spectral specifications is restricted.

In certain embodiments of the invention the excitation light sources may be fixed in the excitation module while the ends of the first light guides next to the excitation light sources may be rotated relative to the excitation light sources. The other ends of the light guides stay affixed to the reaction regions in this embodiment. In this way the same measurement sequence as displayed in FIG. 9 can be applied to the reaction regions.

In certain embodiments of the invention the mono color light sources (e.g., the LEDs) can be fixed within the excitation module instead of being mounted on a rotary wheel. In such embodiments the light is transferred to the first light guides by an optical device (e.g. prisms, optical microelectromechanical systems (MEMS), mirrors). This device enables to route the light of each light source to each first light guide in such a way that the same advantageous measurement sequence as shown in FIG. 9 may be applied. Different embodiments of such an optical device are conceivable. The whole device may be rotated in order to route the light from the light sources to the first light guides or the device itself may contain optical switches (e.g. switchable mirrors) which route the light from the different light sources to the first light guides.

Apparatuses according to the invention may in certain embodiments further comprise at least one control light guide for monitoring the power of the light sources. Such a light guide is combined with one of the first light guides which is affixed to a certain site in the excitation module and leads to a separate detector. In doing so, the power of the light source can be monitored simultaneously with the excitation of the respective reaction region. In certain embodiments more than one control light guide may be present each of them leading to separate detectors. Hereby, each light source can be monitored simultaneously during the excitation of each reaction region.

The apparatus as described above may be used in an instrument for amplifying and detecting nucleic acids. Besides the apparatus for emitting and detecting light such an instrument at least comprises a sample placed in one of the at least two reaction regions comprising a plurality of components and detectable markers capable of generating light emission upon excitation, which is different when a target is present from when a target is not present and a device for subjecting the at least one sample to amplification and/or melting reactions. In a certain embodiment the sample may be provided in a vessel that is placed in the reaction region. The apparatus can be combined with a thermal cycler which applies specific temperature cycles to the reaction regions in order to amplify the samples contained in the reaction regions. Besides a thermal cycler and an apparatus according to the invention the instrument may contain means to extract nucleotide acids from blood plasma (e.g., a pipetting device, incubators, wash and separation stations as well as means for loading reagent bottles, reagent racks and sample tubes). Furthermore, such an instrument may be an overall process solution ranging from the nucleotide acid extraction to the quantification of the initial target concentration and encompassing all electronic printed circuit boards (PCBs) along with personal computer and specifically designed software for controlling the process.

The apparatus and the instrument according to the invention may particularly be used in real-time nucleic acid amplification reactions, such a multiplex-PCR applications which comprise more than one target sequence to be processed and the target sequence or the probes specifically hybridizing to the target sequences are labeled with different dye-markers. However, besides fluorescent markers also phosphorescent, chemiluminescent and electro-chemiluminescent markers may be used in an apparatus and/or instrument according to the invention. Besides multiplex PCR applications the apparatus and the instrument according to the invention may also be used in other applications such as hybridization assays, fluorescence in situ hybridization assays using peptide nucleic acid probes, RNA-RNA hybridization assays, protein multiplex assays or other amplification-detection applications such as quantitative PCR, quantitative real-time PCR, ligation-mediated PCR (e.g., multiplex ligation-dependent probe amplification (MLPA), ligase chain reaction), RACE-PCR, asymmetric PCR, etc. In other embodiments, other nucleic acid amplification techniques, such as nucleic acid sequence based amplification (NASBA), strand displacement amplification (SDA), ligase chain reaction (LCR) etc. may be monitored by the apparatus and/or instrument of the invention. Furthermore, the present invention is well suited to monitor nucleic acid melting curve reactions.

In a method for detecting particular specimens in a sample the sample to be examined is provided in a reaction region and comprises at least two detectable markers, wherein each detectable marker emits detectable light when excited with an excitation beam including light of a respective excitation wavelength. The sample is then illuminated with excitation beams of distinct spectra emitted from at least one excitation light source. The emission light emitted from the sample is detected with an emission module while the detectable marker is excited by a respective excitation beam. In particular embodiments particular specimens are nucleic acids. In certain aspects at least one target nucleic acid within the sample is amplified and/or melted.

Such methods using an apparatus and/or an instrument according to the invention are further described by the way of example in the example section.

EXAMPLES

Example 1

The following examples and figures are provided to aid the understanding of the present invention, the scope of which is set forth in the appended claims. It is understood that modifications can be made in the embodiments set forth herein without departing from the spirit of the invention.

A real time multiplex PCR run with an Hepatitis C Virus (HCV) clean target of known concentration and a quantification standard (QS) was performed using two apparatuses according to the invention. In each reaction region, 50 μl PCR reagent mixtures (44.6 μl Master Mix containing an appropriate forward and reverse primer along with 5.4 μl $Mn^{2+}$-buffer per sample) were provided along with 25 μl of the HCV target having a concentration of $1\times10^6$ copies/μl and 25 μl of a quantification standard (QS) at a concentration of 40 copies/μl. The master mix, the $Mn^{2+}$-buffer and the quantification standard are from commercially available reagent kits (Roche cobas TaqMan® HCV Master Mix: Kit no. 58004181, Roche cobas TaqMan® HCV $Mn^{2+}$ Kit no. 52004183, Roche Amplicor® Monitor HCV QS V2.0: Kit no. 58002560 from Roche Diagnostics, Pleasanton, Calif.). The clean targets were labeled with 6-carboxyfluorescein dye (FAM) dye, while the quantification standard (QS) were labeled with hexachloro-fluorescein (HEX) dye. Sixty-two temperature cycles along with one pre cycle and one reverse transcriptase step as shown below were applied to each reaction region using two thermal cyclers. The following table shows the thermal cycler profile that was used for the amplification.

| | nr | Temperature/° C. | Time/sec |
|---|---|---|---|
| Pre cycle | 1 | 50 | 300 |
| Reverse Transcriptase | 1 | 59 | 1800 |
| Denaturation | 2 | 95 | 15 |
| Annealing/Extension | | 58 | 40 |
| Denaturation | 60 | 91 | 15 |
| Annealing/Extension | | 58 | 40 |
| Post cycle | 1 | 40 | 120 |

The heating and cooling ramps for changing of the applied temperatures were selected as 7° C./min. for heating and 5° C./min. for cooling,
The resulting amplification curves are displayed in FIGS. 7 and 8.
Results
FIG. 7 shows the amplification curves of the real time multiplex HCV-PCR run mentioned above. Ten samples containing PCR mixtures were amplified and the signals were measured in the FAM-channel. The data are corrected for the crosstalk caused from the quantification standard labeled with HEX marker dye which is partly excited and detected in the FAM-channel as well. A significant signal increase is an indicator that the target sequence is present. The cycle number where a significant signal increase occurs at is a measure of the initial target concentration. The smaller the cycle number the higher the initial target concentration is. This characteristic cycle number is called elbow number. The determination of this elbow number is a specific property of the type of algorithm which is used to analyze the amplification curves. Different algorithms can determine different elbow numbers of the same amplification curve. The following table shows the elbow numbers of the amplification curves shown in FIG. 7:

| Thermal Cycler nr | Reaction Region nr | Target Elbow nr |
|---|---|---|
| 1 | 2 | 23.3 |
| 1 | 3 | 23.5 |
| 1 | 4 | 23.6 |
| 1 | 8 | 23.3 |
| 1 | 9 | 23.5 |
| 2 | 2 | 23.3 |
| 2 | 3 | 23.4 |
| 2 | 4 | 23.6 |
| 2 | 8 | 23.4 |
| 2 | 9 | 23.6 |

FIG. 8 shows the amplification curves of the quantification standard (QS) of the same real time multiplex HCV-PCR run.

All 10 samples contained besides the PCR mixtures 25 μl of quantification standard as well. The signal was measured in the HEX-channel. The data are corrected for the crosstalk caused from the clean target labeled with FAM marker dye which is partly excited and detected in the HEX-channel as well. A significant signal increase is an indicator that the quantification standard is present. Also for the quantification standard the characteristic cycle number called elbow number was determined using an algorithm analyzing the amplification curves of QS. The following table shows the elbow numbers of the amplification curves shown in FIG. 8:

| Thermal Cycler nr | Reaction Region nr | QS Elbow nr |
| --- | --- | --- |
| 1 | 2 | 32.1 |
| 1 | 3 | 32.6 |
| 1 | 4 | 32.3 |
| 1 | 8 | 32.5 |
| 1 | 9 | 32.6 |
| 2 | 2 | 31.2 |
| 2 | 3 | 31.5 |
| 2 | 4 | 31.4 |
| 2 | 8 | 31.6 |
| 2 | 9 | 31.6 |

The initial target concentration can be calculated with the help of a calibration curve of the elbow number differences between the target and the quantification standard. The following table shows these calculated titers in copies/μl:

| Thermal Cycler nr | Reaction Region nr | Result Target copy/μl |
| --- | --- | --- |
| 1 | 2 | 8.55E+05 |
| 1 | 3 | 1.42E+06 |
| 1 | 4 | 7.40E+05 |
| 1 | 8 | 1.45E+06 |
| 1 | 9 | 1.38E+06 |
| 2 | 2 | 2.66E+05 |
| 2 | 3 | 3.13E+05 |
| 2 | 4 | 2.34E+05 |
| 2 | 8 | 3.88E+05 |
| 2 | 9 | 3.14E+05 |

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

REFERENCE NUMERALS

1 reaction region
11 excitation module
12 excitation light source
13 rotary wheel
21 emission module
22 detector
23 rotary filter wheel
31 first light guide
32 second light guide
41 control unit

What is claimed is:

1. An instrument for amplifying and detecting nucleic acids, comprising:
    a device for subjecting a sample to amplification and/or nucleic acid hybrid melting reactions, wherein the device comprises a thermal cycler, and
    an apparatus for emitting and detecting light, comprising:
        at least two reaction regions, wherein the thermal cycler applies specific temperature cycles to the reaction regions,
        an excitation module comprising a rotary wheel, said rotary wheel comprising at least two excitation light sources capable of providing excitation light of at least two different wavelength spectra,
        at least two first light guides, each first light guide being capable of directing light emitted from one of said excitation light sources to at least one of said reaction regions,
        at least two second light guides, each second light guide being capable of directing light emitted from one of said reaction regions to an emission module,
        an emission module, said emission module being capable of detecting beams emitted from each of the at least two reaction regions separately and simultaneously, said emission module comprising at least two detectors and a rotary filter wheel, said rotary filter wheel being positioned between said at least two second light guides and said detectors, and
        a control unit configured to the activity of said excitation light sources and of said emission module,
    wherein said rotary wheel comprises at least two excitation light sources and said control unit is configured to rotate said excitation light sources relative to the position of said first light guide, allowing at least one of said excitation light sources to emit light to one defined first light guide;
    wherein the rotation of said rotary wheel carrying said excitation light sources and the rotation of said rotary filter wheel of said emission module are electronically coupled and controlled by the control unit; and
    wherein said control unit is configured to rotate said rotary filter wheel in such a manner that for each reaction region, a filter on said rotary filter wheel having a transmission spectrum corresponding to the emission spectrum of light emitted from said reaction region when excited by excitation light is between said detector and said at least two second light guides when said reaction region is excited by said excitation light.

2. The instrument according to claim 1, wherein said excitation light sources are light-emitting diodes (LEDs).

3. The instrument according to claim 1, wherein said first light guide is a single or a bifurcated light guide bundle capable of directing light emitted from one of said excitation light sources to at least two of said reaction regions.

4. The instrument according to claim 1, wherein said excitation light sources are switched off by the control unit while the rotary filter wheel rotates.

5. The instrument according to claim 1, wherein said at least one first light guide is at one end affixed to a position on said excitation module allowing optical contact of one excitation light source with said one first light guide and at the other end is affixed to at least one reaction region, so as to direct light emitted from said excitation light source to a defined position at said at least one reaction region.

6. The instrument according to claim 1, further comprising at least one control light guide for monitoring the power of the light sources.

7. The instrument according to claim 1, wherein:
    said sample is placed in one of the at least two reaction regions of said apparatus; and said sample comprises a plurality of detectable markers capable of generating light upon excitation by light of a wavelength different from that emitted.

8. A method for detecting nucleic acids in a sample, comprising:
providing a sample in one of the at least two reaction regions of the instrument according to claim 1, said sample comprising a plurality of detectable markers capable of generating light upon excitation by light of a wavelength different from that emitted,
amplifying and/or melting at least one target nucleic acid within said sample,
illuminating said sample with excitation light of distinct wavelength spectra emitted from the at least two excitation light sources of said apparatus, and
detecting the emission light emitted from the sample with the emission module of said apparatus.

* * * * *